United States Patent [19]

Howng et al.

[11] Patent Number: 4,758,814

[45] Date of Patent: Jul. 19, 1988

[54] STRUCTURE AND METHOD FOR WIRE LEAD ATTACHMENT TO A HIGH TEMPERATURE CERAMIC SENSOR

[75] Inventors: Wei-Yean Howng; Rong-Fong Huang; Rickey G. Pastor, all of Albuquerque, N. Mex.

[73] Assignee: Motorola, Inc., Schaumburg, Ill.

[21] Appl. No.: 803,469

[22] Filed: Dec. 2, 1985

[51] Int. Cl.⁴ ............................................. H01L 7/00
[52] U.S. Cl. .................................... 338/34; 338/309; 338/314; 338/329
[58] Field of Search ............... 338/22, 25, 34, 35, 338/308, 309, 314, 324, 329, 333, 334; 422/94, 98; 29/610 R

[56] References Cited

U.S. PATENT DOCUMENTS

| | | | |
|---|---|---|---|
| 2,836,885 | 6/1958 | Macdonald et al. | 29/472.9 |
| 3,339,267 | 3/1967 | Bronnes et al. | 29/473.1 |
| 3,728,660 | 8/1973 | Finney | 338/22 R |
| 3,767,370 | 9/1973 | Ornstein | 29/195.5 |
| 3,929,426 | 4/1975 | Blust et al. | 29/195 |
| 3,970,235 | 3/1976 | Blust et al. | 228/122 |
| 3,975,307 | 8/1976 | Matsuo et al. | 338/22 R X |

FOREIGN PATENT DOCUMENTS

| | | |
|---|---|---|
| 559434 | 12/1958 | Canada . |
| 47-28590 | 1/1972 | Japan . |
| 0022398 | 6/1974 | Japan ................................ 338/308 |
| 0108703 | 8/1980 | Japan ................................ 338/308 |
| 56-119959 | 2/1983 | Japan . |
| 0161978 | 4/1983 | Japan . |
| 0095671 | 7/1983 | Japan . |
| 318435 | 3/1971 | U.S.S.R. . |

OTHER PUBLICATIONS

"High Temperature Metal Ceramic Seals", Ceramic Age, vol. 63-64, No. 4, Apr., 1957.

Primary Examiner—C. L. Albritton
Attorney, Agent, or Firm—Charles L. Warren

[57] ABSTRACT

A first layer of titanium or tin is vapor deposited upon opposing major surfaces on the ceramic sensor. A second layer consisting of platinum, palladium or ruthenium is deposited over the first layer. The structure is then preferably annealed in air in order to crystallize the external layer to roughen the exterior surface and enhance adhesion. Lead wires, preferably made of Nichrome, are attached to the opposing surfaces by applying a conductive paste to the wire and surface functions, and firing the structure. The conductive paste provides a relatively low resistance, strong, mechanical bond between the lead wires and the roughened external surfaces of the structure. The first layer facilitates bonding of the second layer to the ceramic. The first and second layers cooperate to protect the ceramic from the potentially harmful glass frit contained in the conductive paste.

6 Claims, 1 Drawing Sheet

STRUCTURE AND METHOD FOR WIRE LEAD ATTACHMENT TO A HIGH TEMPERATURE CERAMIC SENSOR

BACKGROUND OF THE INVENTION

This invention is directed to a method for securing wire leads to a high temperature ceramic sensor without injuring the sensor or substantially affecting its performance. This invention is also directed to the lead attachment structure which results from the method.

An article entitled "High Temperature Metal Ceramic Seals" in *Ceramic Age,* Vol. 63–64 No. 4, April, 1954, states that three processes have been developed for bonding metal to ceramic. The so-called "Telefunken" process consists of bonding molybdenum powder to the ceramic and then brazing with silver. A second hydride method uses a layer of $TiH_2$ or $ZrH_2$ on the ceramic followed by a silver, copper or lead braze. The bond in this method is formed when the hydride is thermally decomposed. In the third method, a bond is effected by melting on the ceramic an alloy of zirconium or titanium and a brazing metal such as silver or copper.

Japanese Application No. 56-119959 published Feb. 7, 1983 entitled "Production of Ceramic Sensor" describes the production of a ceramic sensor for measuring the density of oxygen in a gas. A paste of a high melting point metal such as platinum is applied to the ceramic sensor and forms electrodes thereon.

In U.S. Pat. No. 3,339,267 issued Sept. 5, 1967 to R. L. Bronnes et al. entitled "Metallizing Non-Metals", the preferred process consists of cathodic sputtering a layer of tantalum onto the ceramic, and then sputtering a layer of platinum over the tantalum layer. A wire lead is soldered to the platinum to establish connection with the ceramic material.

An examined Japanese document No. 47-28590 published in 1972 is directed to joining metallic bodies plated with copper to a ceramic body by metallizing the surface of the ceramic with nickel or a nickel alloy and heating it 780–850 degrees C. in a non-oxidizing atmosphere.

Although various ways have been used to attach wire leads to ceramic sensors, serious problems arise when the attachment structure and sensor must function at high temperatures, i.e., approaching 600 degrees C. A good bond (adhesion) of the lead to the sensor is necessary. Also, the attachment method should not significantly change the response characteristic of the sensor nor degrade the ceramic composition. Where the electrical resistance of the sensor varies in response to the sensed parameter, such as temperature or humidity, the resistance of the lead connection structure should be low relative to the resistance range of the sensor. Establishing such a connection to a ceramic sensor which may be subjected to high temperatures presents problems which are addressed by the present invention.

SUMMARY OF THE INVENTION

It is an object of the present invention to provide an improved method and structure for securing wire leads to a ceramic sensor which must withstand operating temperatures up to 600 degrees C.

In accord with the present invention, a first layer of titanium or tin is vapor deposited upon opposing major surfaces of the ceramic body of the sensor. A second layer consisting of platinum, palladium or ruthenium is deposited over the previous layer. The structure is then preferably annealed in air in order to crystallize the external layer. This annealing step roughens the exterior surface to enhance adhesion. Lead wires, preferably made of Nichrome, are attached to the opposing surfaces by applying a nickel paste to the wire and surface junctions, and firing the structure. The nickel paste provides a relatively low resistance, strong, mechanical bond between the lead wires and the roughened external surfaces of the structure. The first layer facilitates bonding of the second layer to the ceramic. The first and second layers cooperate to protect the ceramic from the potentially harmful glass frit contained in the nickel paste.

DETAILED DESCRIPTION

One aspect of this invention is the discovery of the source of problems encountered in attempting to secure wire leads to a ceramic sensor used at temperatures up to approximately 600 degrees C. Various conductive pastes have been applied to ceramic materials and used in an attempt to bond lead wires to ceramic materials. The conductive pastes consist of metallic or semiconducting metal oxide powder and high melting temperature glass frit. The glass frit acts as an adhesive bonding the conductive powder to the sensing element. However, due to the high mobility of the glass frit at the curing temperature, glass constituents tend to defuse into the ceramic body and produce undesired changes. For example the base resistance of the ceramic material as well as other characteristics may be altered by the penetration of the glass constituents. Also cracking of the ceramic material may result.

The use of an adhesive material not having frits creates other problems. For example, fritless molecular bonding silver has good bonding strength to wire leads and forms a good low resistance contact, but has very little adhesion to the ceramic. Thus, the mechanical strength of the lead attachment is poor.

Because vapor deposition of an electrode on a ceramic surface produces a more dense layer of material than if applied by means of a paste, vapor deposited electrodes form an effective buffer layer preventing subsequently applied conductive adhesives from reacting with the ceramic body. Also, the proper selection of successive films vapor deposited on the ceramic material enables wire leads to be securely attached to the ceramic material and simultaneously provides a good low resistivity connection with the ceramic material.

The lead attachment structure and method according to this invention is believed to be applicable to ceramic materials having various compositions. A specific, but not exclusive, application of this invention is to attach leads to a ceramic material utilized as a temperature sensor having a general composition of $LaCrO_3$ with additions of Ti or Sn. This sensor is described in greater detail in U.S. patent application Ser. No. 732,358 entitled Ceramic Temperature Sensor which is owned by the assignee of the present invention.

Figure 1:
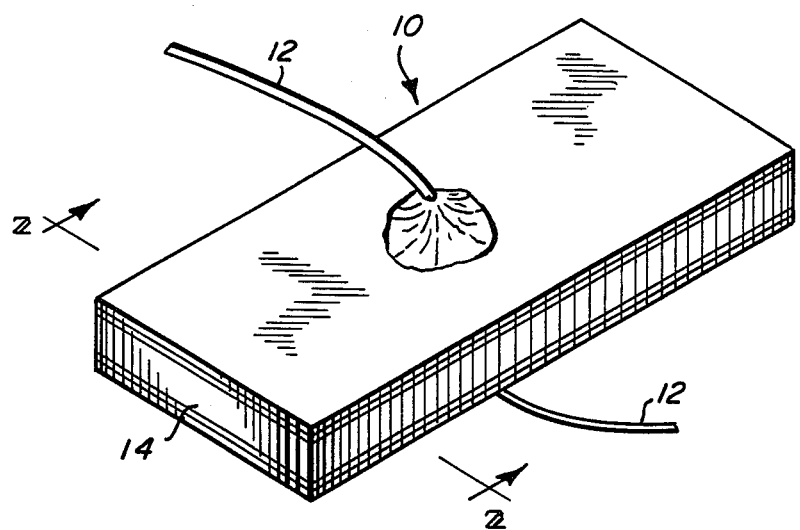
FIG. 1 is a perspective view of a ceramic sensor having wire leads attached according to the present invention.
Figure 2:
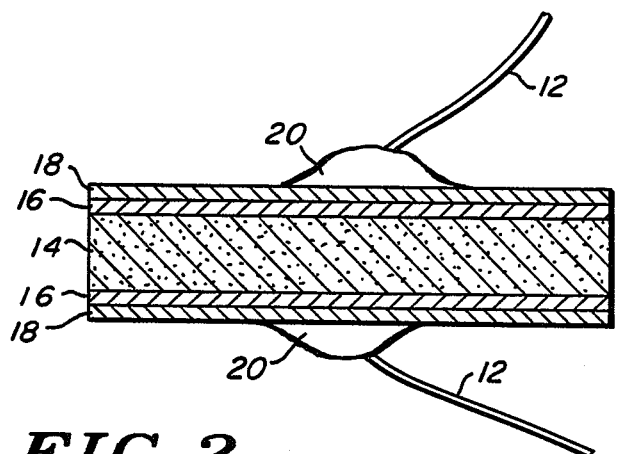
FIG. 2 is a cross sectional view taken along line 2—2 in FIG. 1.

Referring to FIGS. 1 and 2, a lead attachment structure 10 is used to attach wire leads 12 to a plate 14 made of a ceramic material. The attachment structure 10 includes a first layer of material 16 disposed between the ceramic plate 14 and a second layer of material 18, and a material 20 for cementing a lead 12 to the outside layer 18 of material. The two leads 12 are connected respectively to the opposite major surfaces of the ceramic plate 14 by lead attachment structures 10. The leads are utilized to couple the ceramic element to other circuitry which can sense the changes in resistivity of the ceramic plate of material. The particular ceramic material selected will determine what parameters give rise to changes in its resistivity. For example, appropriate ceramic materials can be utilized to sense temperature, humidity, or gases.

The first layer of material 16 consists of titanium (Ti) or tin (Sn) which have been vapor deposited on the major surfaces of the ceramic plate 14. A thickness of 400 angstroms ±40 angstroms has proved suitable for layer 16.

The layer of material 18 consists of platinum (Pt), palladium (Pd) or ruthenium (Ru) which is vapor deposited on top of layer 16. This layer of material 18 is preferably greater than 4000 angstroms thick and is preferably within the range of 4000-6000 angstroms.

The cementuous material 20 must be conductive in order to establish electrical continuity between leads 12 and layer 18. This material may consist of a nickel paste which is made of a metallic or semiconducting metal oxide of fine powder and high melting temperature glass frit. The leads 12, which are preferably Nichrome wires, are securely and conductively bonded to layer 18 after the nickel paste has been fired.

The desired elements for use as layer 18 do not adhere vary well to the ceramic plate 14. It has been discovered that the layer 16 bonds strongly to the ceramic plate 14 and to the materials used as layer 18. Also, the adherance of the nickel paste to the surface of layer 18 is enhanced by roughening the surface of layer 18 by annealing the ceramic plate having layers 16 and 18 prior to application of the nickel paste. The annealing crystalizes, and hence roughens, layer 18 and alloys the layers 16 and 18 together.

The following method describes the steps in the manufacture of the lead attachment structure in which titanium and platinum comprise layers 16 and 18, respectively. The thin film layers 16 and 18 may be deposited by any vapor deposition technique such as electron beam deposition. The thin film deposition is conventional in that it is accomplished in an evacuated, i.e. vacuum, chamber in which the plate of ceramic material 14 along with quantities of titanium and platinum are disposed. In electron beam deposition, the beam is first directed to the titanium target to create a vapor of titanium which is deposited as a thin film on the ceramic plate. After depositing a thin film of titanium of approximately 400 angstroms on the major surfaces of the ceramic plate and while maintaining vacuum, the electron beam is utilized to impact the platinum target and deposit a thin film vapor deposited layer of platinum on the previously deposited layer of titanium. After depositing a layer of platinum of approximately 4000-6000 angstroms, the thin film deposition portion of the process has been completed and the chamber can be opened and the ceramic plate removed.

With the thin film layers 16 and 18 present on the ceramic plate, the unit is annealed in air, i.e. oxygen, to crystalize the external platinum surface and alloy the titanium and platinum together to form a solid solution. The annealing is accomplished at approximately 900-1000 degrees C. for 2 hours.

Two Nichrome wires are held adjacent the respective platinum surfaces and a small quantity of nickel paste is applied to the wires and platinum surface. While holding the wires adjacent to the platinum surfaces, the ceramic element is fired at approximately 850 degrees C. for 10 minutes in an air environment in order to cure the nickel paste. The conductive nickel within the paste provides a conductive contact between the wire and the platinum surface. The glass frit in the paste adhesively bonds the conductive nickel to the wires and platinum surfaces on the sensor.

The platinum and titanium alloy forms an effective barrier preventing the constituents of the glass frit of the nickel paste from reaching the ceramic plate 14. If an effective barrier were not present, the constituents associated with the glass frit would defuse into the ceramic plate and adversely change the properties of the ceramic material and possibly cause cracking.

The annealing step is also a significant aspect of the present invention in that crystalization of the exterior platinum layer occurs to provide a roughened surface. The increased surface roughness is desired in order to increase adhesion with the glass fritted conductive paste. It is important that the fired nickel paste securely adhere to the platinum surface because the lead wires are captivated solely by the fired paste.

It is also significant that the first and second layers of thin film material are deposited by vapor deposition. The dense relatively uniform layers achieved by this process enable an effective barrier to be created with respect to the glass frit contained in the conductive paste.

Although the present invention has been described and illustrated in the figures, the scope of the invention is defined by the claims appended hereto.

What is claimed is:

1. In a transducer capable of operation at temperatures up to 600 degrees C. including a plate of ceramic material and means for attaching wire leads to the plate the improvement in the lead attaching means comprising:
    a vapor deposited thin film of a first material disposed on first and second surfaces of said plate, said first material selected from the group consisting of titanium and tin;
    a vapor deposited thin film of a second material disposed on said films of first material, said second material selected from the group consisting of platinum, palladium, and ruthenium;
    first and second conductive leads disposed adjacent each film of the second material, respectively; and
    conductive adhesive captivating said first and second leads to the respective films of said second material.

2. The transducer according to claim 1 wherein the external surfaces of said films of the second material have been roughened by annealing which crystalizes said external surface to enhance the bonding of said adhesive to said second material.

3. The transducer according to claim 1 wherein said second material is platinum.

4. The transducer according to claim 3 wherein said first material is titanium.

5. The transducer according to claim 1 wherein said first and second leads comprise Nichrome wires.

6. The transducer according to claim 1 wherein said adhesive comprises a conductive paste containing glass frit.

* * * * *